(12) United States Patent
Zengerle et al.

(10) Patent No.: US 6,855,293 B1
(45) Date of Patent: Feb. 15, 2005

(54) FLUIDS MANIPULATION DEVICE WITH FORMAT CONVERSION

(75) Inventors: Roland Zengerle, Villingen-Schwenningen (DE); Nicolaus Hey, Eschbronn-Mariazell (DE); Holger Gruhler, Tuningen (DE); Michael Freygang, Villingen-Schwenningen (DE); Martin Mueller, Dietingen (DE)

(73) Assignee: Hahn-Schickard-Gesellschaft fuer angewandte Forschung e.V., Villingen-Schwenningen (DE)

( * ) Notice: Subject to any disclaimer, the term of this patent is extended or adjusted under 35 U.S.C. 154(b) by 0 days.

(21) Appl. No.: 09/936,881
(22) PCT Filed: Mar. 22, 2000
(86) PCT No.: PCT/EP00/02542
§ 371 (c)(1),
(2), (4) Date: Dec. 31, 2001
(87) PCT Pub. No.: WO00/56442
PCT Pub. Date: Sep. 28, 2000

(30) Foreign Application Priority Data

Mar. 23, 1999 (DE) .......................... 199 13 076

(51) Int. Cl.⁷ .............................. B01L 3/02; B01L 3/00; B01L 11/00; B01L 9/00; G01N 15/06
(52) U.S. Cl. ........................... 422/100; 422/50; 422/58; 422/68.1; 422/81; 422/82; 422/102; 422/103; 422/104
(58) Field of Search .......................... 422/50, 58, 68.1, 422/81, 82, 100, 102, 103, 104

(56) References Cited

U.S. PATENT DOCUMENTS

| | | | |
|---|---|---|---|
| 5,100,627 A | | 3/1992 | Buican et al. .............. 422/108 |
| 5,508,200 A | | 4/1996 | Tiffany et al. ................. 436/44 |
| 5,593,290 A | | 1/1997 | Greisch et al. .............. 417/478 |
| 5,796,416 A | * | 8/1998 | Silverbrook .................. 347/47 |
| 5,847,105 A | | 12/1998 | Baldeschwieler et al. |
| 5,877,580 A | * | 3/1999 | Swierkowski ............... 310/328 |
| 6,022,482 A | * | 2/2000 | Chen et al. ................... 216/27 |
| 6,055,004 A | * | 4/2000 | Fassler et al. ........... 346/140.1 |

FOREIGN PATENT DOCUMENTS

| | | | |
|---|---|---|---|
| DE | 30 04 555 A1 | 8/1981 | |
| EP | 0 955 084 A1 | 11/1999 | |
| JP | 62-69139 | 3/1987 | ............ G01N/1/00 |
| JP | 4-503249 | 5/1990 | .......... G01N/27/32 |
| JP | 4-251750 | 9/1992 | ............ B41J/2/045 |
| JP | 5-240872 | 9/1993 | .......... G01N/35/08 |
| JP | 07-060972 | 3/1995 | ............ B41J/2/135 |

(List continued on next page.)

OTHER PUBLICATIONS

Stefan Fischer–Fruholz, "The handling of nanoliter samples on a chip," American Laboratory, p. 46–51 (Feb., 1998).

*Primary Examiner*—Jill Warden
*Assistant Examiner*—Brian Sines
(74) *Attorney, Agent, or Firm*—Glenn Patent Group; Michael A. Glenn (57) ABSTRACT

A fluid management apparatus includes a substrate having a first surface and a second surface opposite to the first surface. A plurality of fluid inlets, which are preferably media reservoirs, are formed in a first pattern in the first surface of the substrate. A plurality of fluid outlets, which are preferably nozzles, are arranged in a second pattern, which is different from the first pattern, in the second surface of the substrate. A plurality of fluid ducts formed in the substrate for connecting respective fluid inlets with respective fluid outlets are provided so that a format conversation from the fluid inlets to the fluid outlets is effected. The fluid outlets have opening cross-sections smaller than that of the fluid inlets. Furthermore, the fluid inlets may be arranged in the raster scheme of microtiter plates.

9 Claims, 7 Drawing Sheets

FOREIGN PATENT DOCUMENTS

| | | | |
|---|---|---|---|
| JP | 07116575 A | 5/1995 | |
| JP | 9-504864 | 5/1995 | ......... G01N/33/543 |
| JP | 8-233710 | 9/1996 | ............ G01N/1/36 |
| JP | 2000-509651 | 8/1998 | ........... B05B/12/00 |
| JP | 2001-520380 | 4/1999 | .......... G01N/33/00 |
| JP | 11-247763 | 9/1999 | ........... F04B/43/06 |
| JP | 337189 | 9/2003 | |
| WO | WO93/09668 | 5/1993 | |
| WO | WO93/10910 | 6/1993 | |
| WO | WO97/01393 | 1/1997 | |
| WO | WO97/45730 | 12/1997 | |
| WO | WO98/26179 | 6/1998 | |
| WO | 98/36832 | 8/1998 | ............ B01L/3/02 |
| WO | WO98/51999 | 11/1998 | |
| WO | 98/51999 | 11/1998 | .......... G01D/15/14 |

\* cited by examiner

FLUIDS MANIPULATION DEVICE WITH FORMAT CONVERSION

BACKGROUND OF THE INVENTION

1. Field of the Invention

The present invention relates to a fluid management apparatus which provides format conversion between a plurality of fluid inlets and a plurality of fluid outlets and is suitable, for example, for use in a dispensing head.

The fluid management apparatus in accordance with the invention can be advantageously used, for example, in the dispensing head of an apparatus for applying at least one microdroplet to a substrate, with which a plurality of microdroplets can be applied to a substrate. In particular, the fluid management apparatus in accordance with the invention is suitable for being used in the production of so-called biochips, in which a plurality of different analytes are applied to a substrate in order to detect a different substances in an unknown sample. In addition, the present invention is suitable for implementing a format conversion between microtiter plates having different raster dimensions.

The increasing decryption of genomes of humans, animals and plants provides for a multitude of new possibilities, ranging from diagnosis of genetic diseases to a substantially accelerated search for active substances which are interesting from a pharmaceutical point of view. The above-mentioned biochips will in the future be used, for example, to examine food stuffs with regard to a multitude of possible, genetically manipulated components. In a further field of application, such biochips may be used to determine the exact genetic defect in genetic diseases so as to derive therefrom the ideal strategy for treating the disease.

The biochips which may be used for such applications typically consists of a carrier material, i.e. a substrate, onto which a multitude of different substances are applied in the form of a raster. Typical raster spacings in the array range from 100 $\mu$m to 1,000 $\mu$m. The diversity of the different substances, which are referred to as so-called analytes, on one biochip ranges from only a few different substances to several 100,000 different substances per substrate, depending on the application. With each of these different analytes, a specific substance can be detected in an unknown sample.

If an unknown sample liquid is applied to a biochip, certain analytes show reactions which can be detected by means of suitable methods, i.e. by fluorescence detection. Here, the number of the different analytes on the biochip corresponds to the number of the different components in the unknown sample liquid, which can be analyzed simultaneously using the respective biochip. Such a biochip is a diagnose tool with which an unknown sample can be examined simultaneously and specifically with regard to a multitude of constituents.

2. Description of Prior Art

Currently, three principally different methods are known for applying the analytes onto a substrate so as to produce such a biochip. These methods are employed alternatively, depending on the number of biochips required or on the number of analytes required per chip.

The first method is referred to as "contact printing" wherein a bundle of steel capillaries is used, the interior of which is filled with different analytes. This bundle of steel capillaries is stamped onto the substrate. When the bundle is lifted off, the analytes will remain attached to the substrate in the form of microdroplets. In this method, however, the quality of the printing pattern is very strongly determined by the action of capillary forces and therefore depends on a multitude of critical parameters, for example on the quality and the coating of the surface of the substrate, on the exact geometry of the nozzle and, above all, on the media used. In addition, the method is highly susceptible to contamination of the substrate and of the nozzles. This above-described method is suited for a variety of analytes of up to several 100 per substrate.

In a second method for producing biochips, the so-called "spotting", mostly so-called microdispensers are employed which are capable, similarly to ink printers, of firing individual microdroplets of a liquid onto a substrate upon a corresponding control command. Such a method is referred to as "drop-on-demand". Such microdispensers are commercially available from several companies. The advantage of this method is that the analytes may be applied onto a substrate without direct contact, the influence of capillary forces having no significance. However, a major problem is that it is very expensive and rather difficult to arrange a multitude of nozzles, which are all supplied with different media, in parallel or in an array. The limiting element here is actuating means as well as media logistics, which are not miniaturizable to the desired extent.

As a third method for manufacturing biochips the so-called "synthesis method" is currently used, wherein the analytes, which typically consist of a chain of nucleic acids which are attached to one another, are chemically produced on the substrate, i.e. synthesized. For demarcating the spatial position of the various analytes, methods are used such as are known from microelectronics, for example lithography methods using mask techniques. This synthesis method is by far the most expensive one among the methods mentioned, which allows, however, to produce the largest variety of analytes on a chip, in the order of magnitude of 100,000 different analytes per substrate.

From WO-A-93/09668, methods are known of forming polymers having different monomer sequences on a single substrate, wherein, via a plurality of channels formed in a channel block, monomers are brought to selected regions for synthesizing polymers at these regions. For this purpose, the channel blocks comprise channels which are opened toward the outside in a surface and which comprise an inlet and an outlet formed in the opposite surface of the channel block. A desired reagent is supplied to the channel via the inlet opening, whereas a vacuum pump is connected to the outlet opening.

WO-A-97/45730 relates to a method and apparatus for supplying solutions to an array of cells. To this end, an array of cells is formed on a substrate. A further substrate has recesses and microchannels connected to the recesses, which channels enable supplying a fluid to the recesses. The cells are introduced into the recesses whereupon solutions are brought into the recesses through the channels for treating the cells. The microchannels are connected with microcapillary tubes via which solutions can be supplied, for example using a microtiter plate.

SUMMARY OF THE INVENTION

It is the object of the present invention to provide a fluid management apparatus which allows applying microdroplets from a plurality of fluid reservoirs to a substrate in a predetermined pattern in a cost-effective and accurate manner.

According to a first aspect of the invention, this object is achieved by a fluid management apparatus comprising:

a substrate having a first surface and a second surface which is opposite to the first surface;
a plurality of fluid inlets which are formed in a first pattern in the first surface of the substrate and comprise first opening cross-sections;
a plurality of fluid outlets which are formed in a second pattern, which is different from the first pattern, in the second surface of the substrate and comprise second opening cross-sections which are smaller than the first opening cross-sections; and
a plurality of fluid ducts formed in the substrate, each fluid duct connecting a fluid inlet with a fluid outlet such that each fluid outlet is in fluidic communication with exactly one fluid inlet.

According to a second aspect of the invention, this object is achieved by a fluid management apparatus comprising:
a substrate having a first surface and a second surface which is opposite to the first surface;
a plurality of fluid inlets which are formed in a first pattern in the first surface of the substrate and which are arranged in the raster scheme of microtiter plates;
a plurality of fluid outlets formed in a second pattern, which is different from the first pattern, in the second surface of the substrate; and
a plurality of fluid ducts formed in the substrate, each fluid duct connecting a fluid inlet with a fluid outlet such that each fluid outlet is in fluidic communication with exactly one fluid inlet.

The present invention therefore provides a fluid management apparatus which provides a format conversion between a first pattern and a second pattern. The automatic format conversion is effected by the arrangement of the flu id inlets, the fluid outlets and by the media ducts. The substrate of the fluid management apparatus in accordance with the invention is preferably manufactured micromechanically, i.e. by silicon processing techniques or injection molding techniques, for example.

The fluid inlets formed in the first surface of the substrate of the fluid management apparatus in accordance with the invention are preferably designed as fluid reservoirs which are arranged in the raster scheme of common microtiter plates which comprise, for example, 96, 384, 1536, etc., chambers. Thus, the fluid reservoirs can be automated using conventional laboratory pipetting machines and can be charged in parallel. In contrast, the nozzles are preferably arranged in the relatively narrow raster in which analytes are to be applied onto microarrays or biochips.

The present invention is based on the realization that in the above-mentioned known methods, one positioning process is necessary, respectively, to print liquids taken from reservoirs which are spaced very far apart onto a substrate in narrow spacings. In accordance with the invention, the fluid management apparatus may be charged using standard automatic devices, wherein, even though the liquid is filled into openings (reservoirs) which are spaced "far" apart from each other, microdroplets can be printed simultaneously and closely adjacent to one another without any further positioning process.

The fluid management apparatus in accordance with the invention may serve as a dispensing head or may be advantageously used in such a dispensing head. The dispensing head preferably has liquid storage areas which are in fluidic communication with the nozzle openings of the fluid management apparatus, such that by applying acceleration to the dispensing head, microdroplets can be driven out of the nozzle opening due to the inertia of a liquid present in the liquid storage areas. Here, the liquid storage area can preferably be formed by a raising main extending from the nozzle opening in a direction which is opposite to the direction in which the microdroplets can be driven out of the dispensing head.

The present invention therefore provides a fluid management apparatus with which, for example, biochips can be produced in high numbers and at low cost. Also, the fluid management apparatus in accordance with the invention is suitable for carrying out a format conversion between microtiter plates having different raster schemes.

In particular, the invention advantageously allows the implementation of a dispensing head in which microdroplets are driven out of the dispensing head by mechanical acceleration which is applied to a dispensing head by an external mechanical system. In the external mechanical system, which represents a driving means, any suitable apparatus can be used, for example piezo bending converters, piezo stacks, pneumatic drives and the like. Here, inertia forces act on a liquid which is located in areas which are in fluidic communication with the nozzle opening, i.e., for example, the nozzle itself, a media duct and a reservoir. Since the liquid is not in rigid communication with the dispensing head, an acceleration of the liquid relative to the dispensing head carrying the liquid results due to the inertia forces. Thus, the liquid starts moving relative to the dispensing head. If this relative movement between the liquid in the nozzle and the nozzle opening is large enough, a microdrop tears off at the nozzle. The size of this drop is determined by the amount and duration of the acceleration of the dispensing head, by the quantity of the liquid mass whose inertia effects the ejection, by the nozzle diameter, and by the flow resistance of the movement of the liquid in the dispensing head. The direction of the acceleration applied to the dispensing head must be oriented such that the liquid is hurled out of the nozzle due to its inertia rather than withdrawing into liquid storage areas or media ducts in the dispensing head.

Using the fluid management apparatus in accordance with the invention, a plurality of microdroplets are applied onto a substrate simultaneously, so that for example a biochip wherein different biologically relevant substances are applied onto a substrate in a regular pattern can be produced reliably and at low cost. Due to the acceleration of the dispensing head, one microdroplet, respectively, is simultaneously driven out of each individual nozzle in a dispensing head, with the inertia of the liquid being utilized.

Here, varying accelerations can be applied to the dispensing head comprising the fluid management apparatus in accordance with the invention so as to effect the ejection of droplets of liquid. One possibility is to accelerate the dispensing head, from a position adjacent to the substrate, very strongly from its resting position in order to achieve a movement of the dispensing head away from the substrate. An alternative possibility is to abruptly decelerate the dispensing head from a continuous movement toward the substrate, this decelerating being supportable, for example, by a mechanical stop. In addition, it is also possible to provide, for the dispensing head, a fixture which is mechanically sufficiently rigid and is excited in the range of the natural frequency of the same, such that the fixture and therefore the dispensing head carry out a semioscillation. In this case, maximum acceleration occurs at the point of regression of the oscillation, so that the fixture and the dispensing head are arranged such that the dispensing head arranged adjacent to the substrate at the point of regression of the oscillation.

If such a dispensing head is abruptly decelerated immediately before the substrate from a movement toward the substrate, the liquid retains its movement due to its inertia and due to the fact that it is not in rigid communication with the dispensing head, and is hurled out of the nozzle onto the substrate. If a resting dispensing head which is situated immediately above a substrate is suddenly accelerated away from the substrate, the liquid cannot follow this movement due to its inertia and due to the fact that it is not in rigid communication with the dispensing head, and leaves the nozzle in the opposite direction to that of the movement of the dispensing head, which is caused by the acceleration away from the substrates, and will initially be suspended in space before the drops fall onto the substrate due to the gravitational force. Here, an apparatus may be provided for generating an electrostatic field between the dispensing head and the substrate in order to thereby support the application of the droplets onto the substrate.

In both above-mentioned cases it is favorable for the acceleration of the dispensing head to occur in a position where the distance between the nozzles in the dispensing head and the substrate is very small. Then it is ensured that, when satellite drops form, respectively, during the detachment of the microdrops, these will unite with the mother drop on the substrate at the latest. Due to the small distance it is ensured that the satellite drops will end up on the mother drop even if they have left the nozzle at a slightly different angle.

BRIEF DESCRIPTION OF THE DRAWINGS

In the following, preferred embodiments of the present invention will be explained in more detail with reference to the attached drawings, in which:

FIGS. 5, 6, 7, 7a), 7b) and 8 diagrammatically show cross-sectional views of examples of alternative fluid management apparatus in accordance with the invention.

DESCRIPTION OF PREFERRED
EMBODIMENTS OF THE INVENTION

With reference to the figures, preferred embodiments of the present invention with regard to a dispensing head will be described in more detail below. However, it is evident that the principles explained may also apply, in the same manner, for other fluid management apparatus, to example means for format conversion between microtiter plates having different raster schemes.

Figure 1:
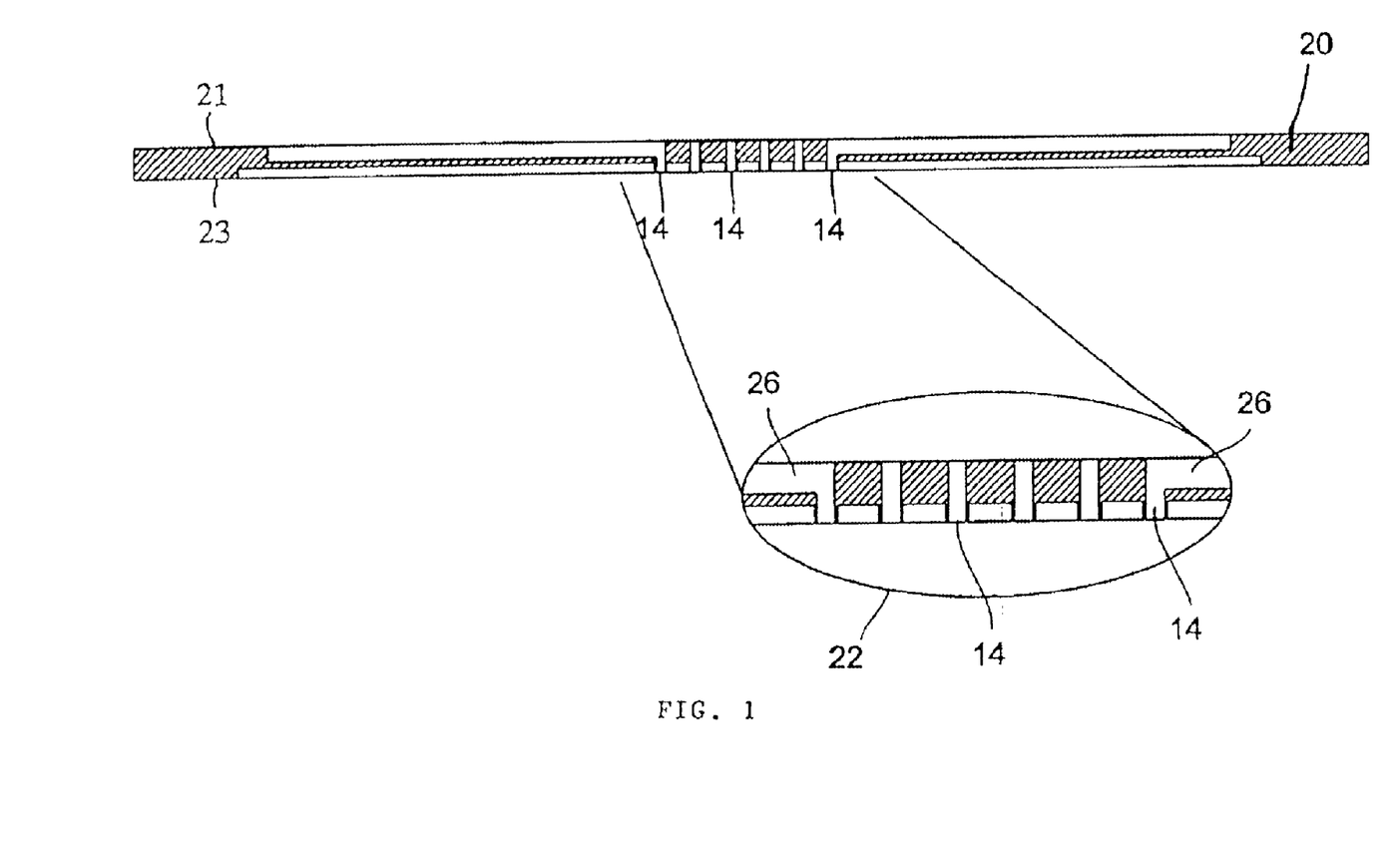
FIG. 1 diagrammatically shows a cross-sectional view of an embodiment of a fluid management apparatus in accordance with the invention in the form of a dispensing head.
Figure 2:
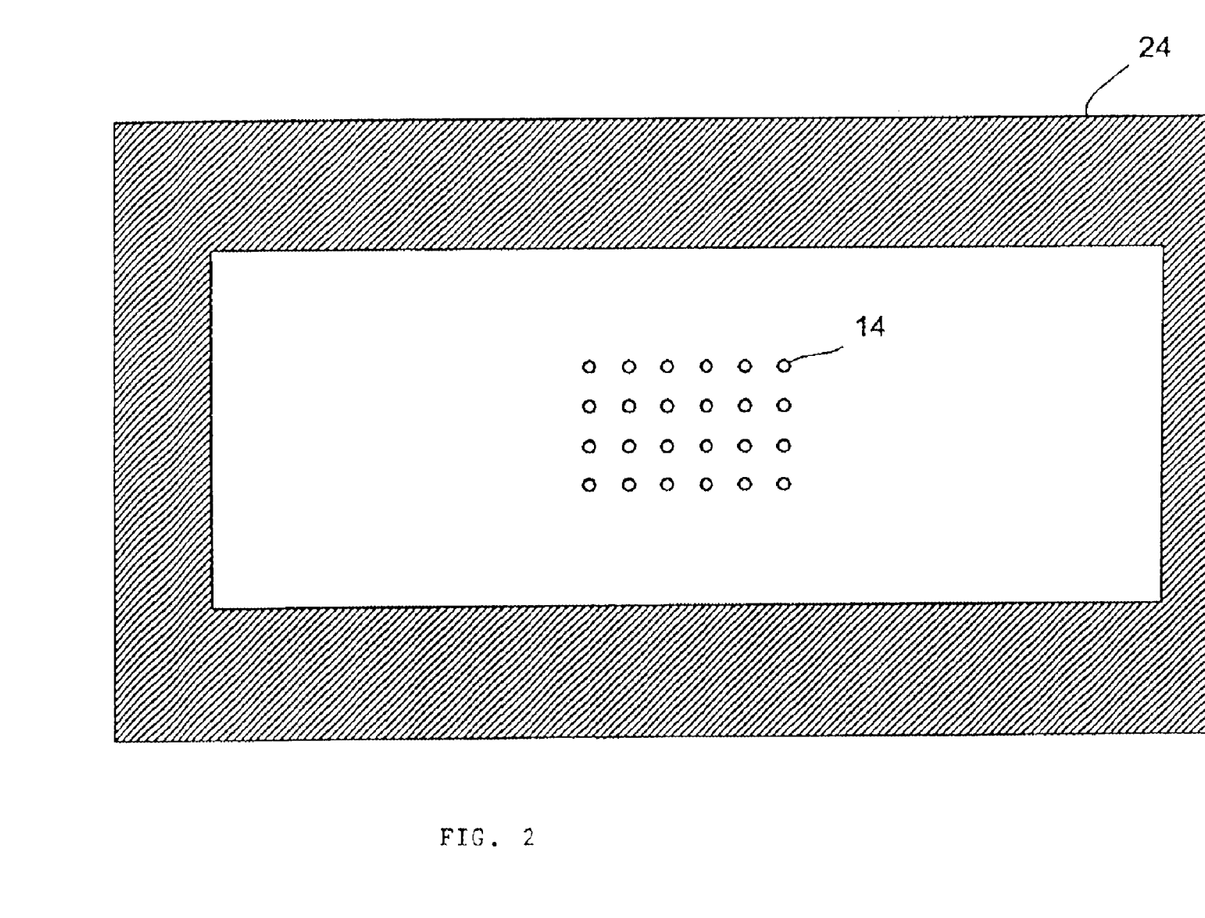
FIG. 2 diagrammatically shows a bottom view of the dispensing head shown in FIG. 1.
Figure 3:
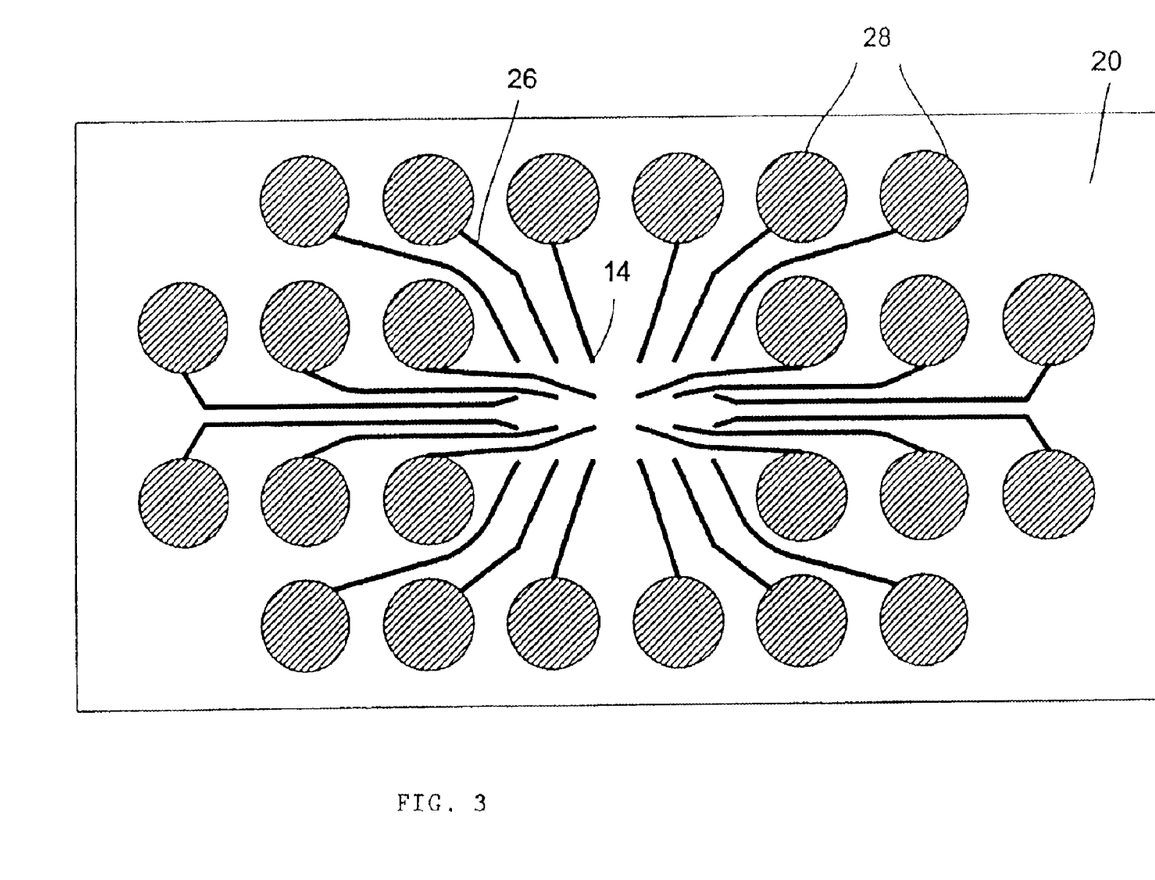
FIG. 3 diagrammatically shows a top view of the dispensing head shown in FIG. 1.

With reference to FIGS. 1 to 3, a preferred embodiment of the fluid management apparatus in accordance with the invention, which may be a dispensing head, will be further explained below. The dispensing head may be a chip, for example, which has been produced using the methods of silicon micromechanics. Alternatively, the dispensing head may be formed from a plastic or a polymer using an injection molding technique. Further, the dispensing head may consist of a silicon-glass compound, a metal or a ceramic.

A diagrammatic cross-sectional view of such a chip, i.e. a fluid management apparatus in accordance with the invention, is shown in FIG. 1 and indicated by reference numeral 20, FIG. 1 further containing an enlarged view 22 of the area where the nozzle openings 14 are arranged. The chip or the substrate 20 has a first surface 21 and a second surface 23. The nozzles 14 are microstructured in the second surface 23, i.e. in the bottom of chip 20 in the figures, and are exposed compared to the surrounding silicon surface. FIG. 1 shows six nozzles 14 arranged adjacent to each other, a bottom view of the chip with nozzles 14 structured in the bottom of the same being shown in FIG. 2, where it can be seen that the embodiment shown of a dispensing head contains twenty-four nozzles. As can also be seen, in the embodiment shown, the nozzles are exposed compared to the surrounding silicon surface, the dispensing head being surrounded by a border 24 in the bottom view of the same. In the embodiment shown, nozzles 14 are connected, via fluid ducts or media ducts 26, to media reservoirs 28 (FIG. 3), which are also integrated on the chip. Media reservoirs 28 are structured in the first surface 21 of chip 20. Due to the representation as a cross-section, the four interior media ducts can merely be seen as vertical ducts in FIG. 1.

A diagrammatic top view of the dispensing head 20 shown in FIG. 1 is illustrated in FIG. 3, with twenty-four media reservoirs 28, which are connected with respective nozzles 14 via media ducts 26, being illustrated. In the embodiment illustrated the media reservoirs 28 are structured in the surface of the chip forming the dispensing head, this surface opposing nozzles 14. Media reservoirs 28 are preferably adapted such that they can be charged with liquids in an automated manner using standard pipetting automatic devices. For this purpose, the same may have diameters and spacings which are identical to those of the chambers of a known microtiter plate, for example a 348-well microtiter plate. The liquid from the media reservoirs 28 is preferably drawn to the nozzles 14 via the media ducts 26 by capillary forces. Here, the media ducts 26 serve to provide the nozzles 14, which are closely adjacent to each other, with liquid from a larger reservoir 28. The charging of the structure can be supported by active control, for example by applying external pressure.

The nozzles described with reference to FIGS. 1 to 3 may have, for example, a diameter of 200 $\mu$m, it being possible for the media ducts 26 to also have a width of 200 $\mu$m. Thus, twenty-four nozzles can easily be arranged in an array of six by four nozzles, as can be seen in FIG. 2, at a mutual distance of 1 mm. The limiting factor regarding the number of nozzles that can be arranged in an array is the width of the interconnection channels which connect the nozzles with the reservoirs. These interconnection channels must be guided to the outside between the nozzles. In case of a reduction of the width of these channels, 48, 96 or more nozzles can be arranged on a dispensing head.

Figure 4:
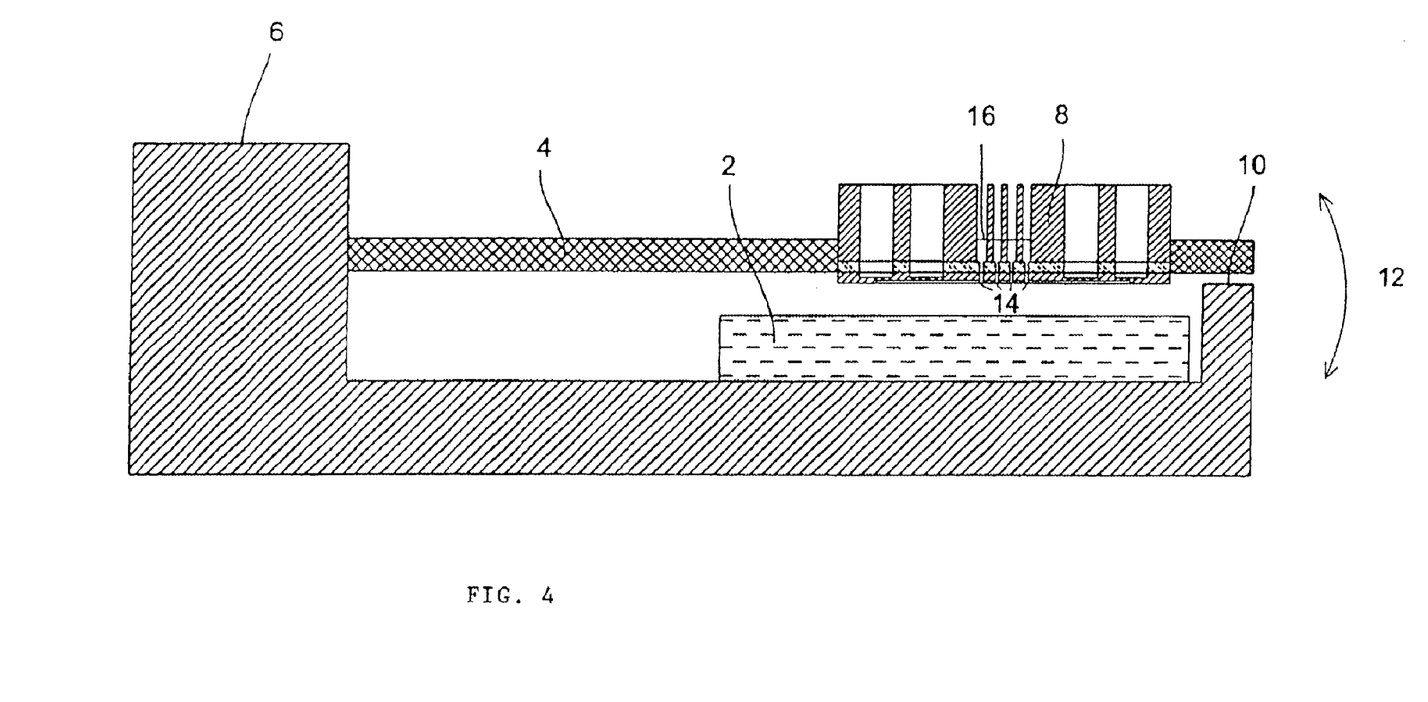
FIG. 4 diagrammatically shows an example of a use of the fluid management apparatus gin accordance with the invention in an apparatus for applying microdroplets onto a substrate.

FIG. 4 illustrates a diagrammatic cross-sectional view of an apparatus for applying microdroplets onto a substrate 2, wherein the fluid management apparatus in accordance with the invention can be used. As is shown in FIG. 4, a piezo bending converter 4 is unilaterally clamped at a fixture 6 a dispensing head 8 being mounted at the non-clamped end of the piezo bending converter 4. The dispensing head 8 may be formed by a fluid management apparatus in accordance with the invention.

As can be seen in FIG. 4, the fixture 6 is configured such that the same forms a stop 10 by means of which a movement of the piezo bending converter 4 and thus of the dispensing head 8, which movement is diagrammatically indicated by arrow 12, is limited in the downward direction in the illustration of FIG. 4. The dispensing head 8 has a plurality of the nozzle openings 14 above which an amount of liquid is arranged, respectively, as is diagrammatically indicated by the reference numeral 16 and is explained in more detail below.

During operation, the piezo bending converter 4 is, driven so as to move the dispensing head 8 downwards. This movement is ended abruptly when the right end of the piezo bending converter impinges upon the stop 10, so that a strong negative acceleration is applied to the dispensing head 8. Due to this strong negative acceleration, the inertia of the amounts of liquid 16 which are arranged above the nozzle openings 14 causes a microdroplet to be driven out of the nozzle openings 14 and to impinge upon the substrate 2. If these are different liquids in each case, an array of analytes can be produced on the substrate 2 by means of the plurality of nozzle openings 14. As is diagrammatically shown in FIG. 4, it is advantageous that the dispensing head 8 be arranged immediately adjacent to the substrate at the time when the negative acceleration is applied to the same, in order to enable exact positioning of the microdroplets on the substrate 2 and to cause any potential satellite droplet portions to unite with the mother droplet.

The actual profile of the acceleration applied to the dispensing head can be varied via the edge steepness of the voltage signal with which the bending converter is driven. The amplitude of the movement can simply be adjusted via the length of the piezo bending converter or the amplitude of the voltage signal, wherein a stop 10 can be provided, as is shown in FIG. 4, for supporting the abrupt decelerating of the dispensing head. Alternatively, it may be sufficient to effect sudden deceleration of the dispensing head via a high-slope electric control signal.

In addition to the piezo bending converter illustrated in FIG. 4, a piezo stack actuator may be used, for example, as a driving means for sudden acceleration of the dispensing head. In this case, however, it is recommendable to increase the path length of the actuator, which is typically between 20 $\mu$m and 100 $\mu$m, via a mechanical lever. On the whole it is advantageous for the entire distance by which the dispensing head is moved to be larger than the diameter of the drop which is to be hurled out of the nozzle. Otherwise, in the event of very small movements there is a danger that a drop which is already outside the nozzle is drawn back into the nozzle before it can tear off completely. Further, it may be advantageous to move the dispensing head, after the abrupt deceleration and after the same has moved toward the substrate, away from the substrate again at high speed so as to positively influence the tearing off of the drop.

Overall it is advantageous for the dispensing head 8 and the mechanical driving means, which is formed by the piezo bending converter 4 and the fixture 6 in the embodiment in FIG. 4, to be adapted in a modular fashion so that the dispensing head can easily be replaced.

In order to avoid that the liquids from different media ducts mix with each other in the area of the nozzles, the top face of the chip can be covered either by a hydrophobic layer (not illustrated), by a film or by a further silicon chip or glass chip bonded onto the top face of the chip.

Figure 5:
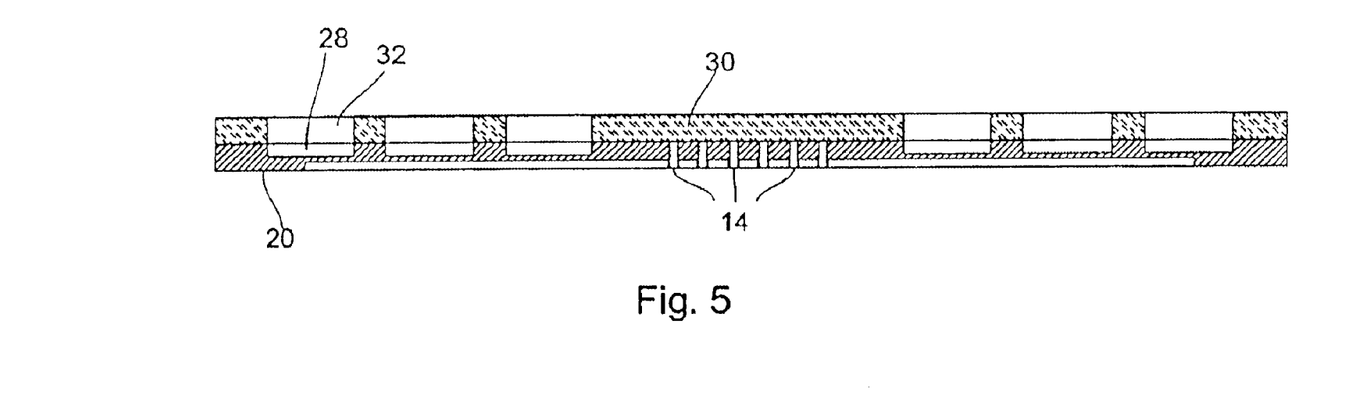

Such a cover chip 30 is shown in FIG. 5, it being recognizable that the cover chip 30 has openings 32, allowing a charging of the media reservoirs 28. It may be preferred to use, as the cover layer 30, an elastic film which may be advantageous in comparison with a rigid cover plate due to its resilience.

Figure 6:
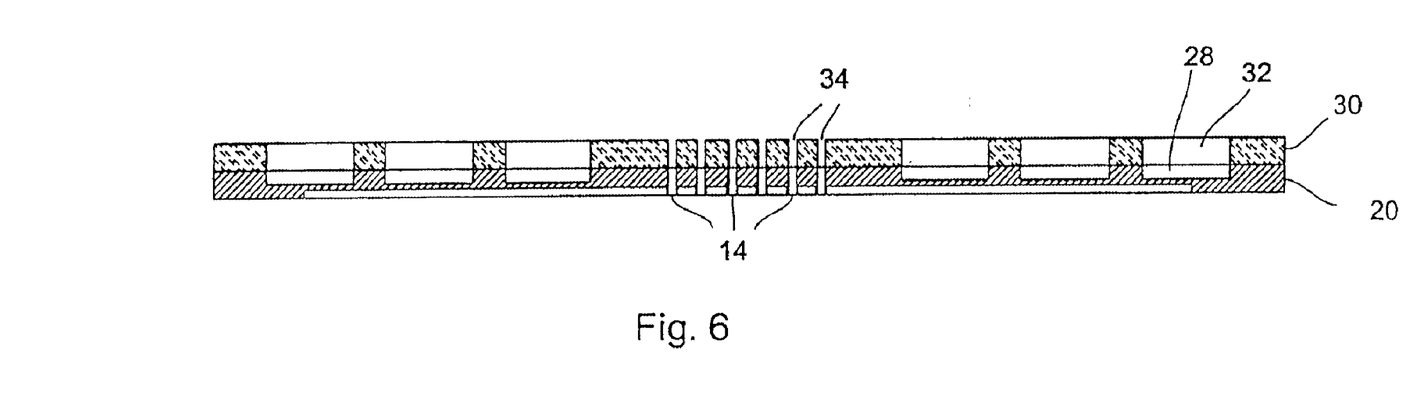
Figure 7:
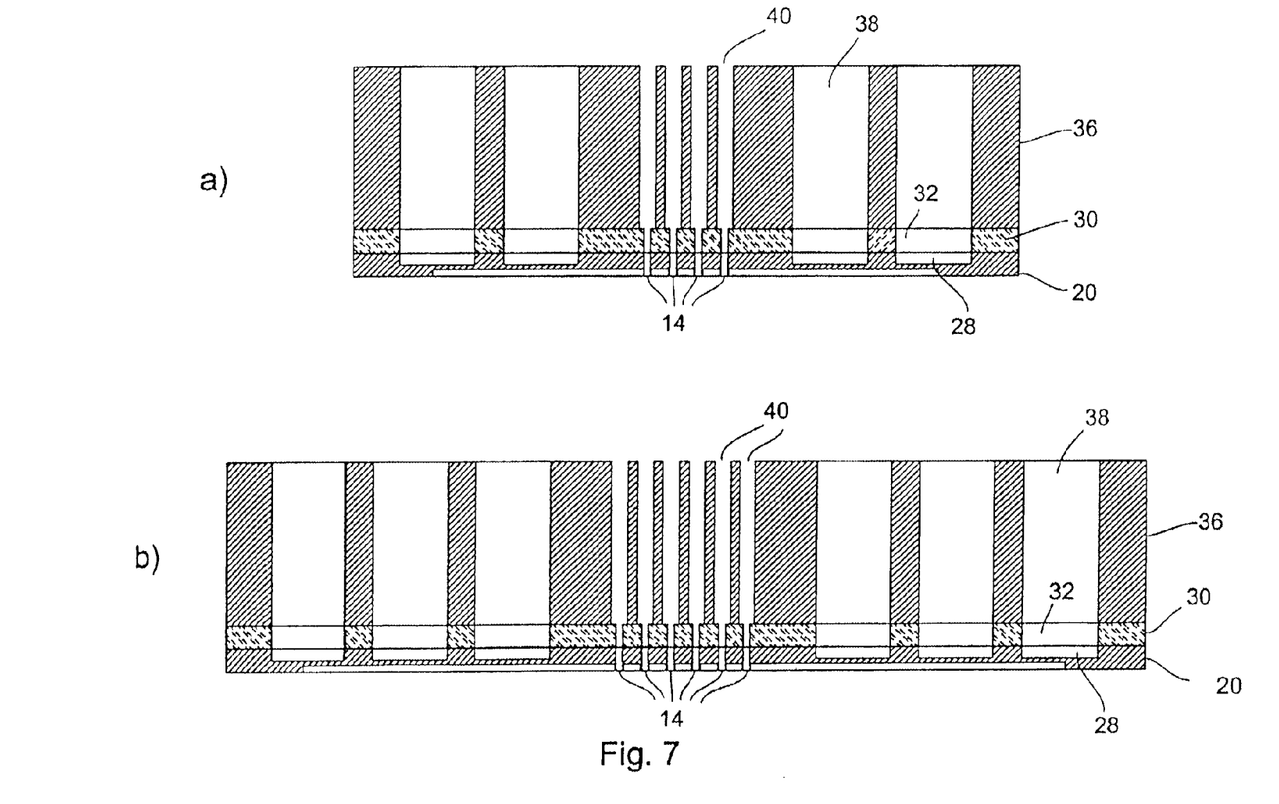

In the above-described embodiments of a dispensing head, the dispensing quality may depend on the flow resistances of the liquid in the media ducts. Therefore, it may be preferred to enlarge, in the dispensing head, the mass of liquid which is situated directly above the nozzles so as; to achieve that the dispensing quality becomes independent of the flow resistances of the media ducts. Embodiments of dispensing heads in which such an enlargement of the liquid mass above the nozzles has been realized are shown in; FIGS. 6 and 7. As can be seen in FIG. 6, an axial rising pipe 34 is arranged above the nozzles 14, 9 respectively, which extends opposite to the ejection direction. These rising pipes may be tied, via a T-shaped connection (not illustrated) near the nozzle, to the media ducts which remain unchanged at the top side of the chip. The rising pipes 34 become charged with liquid from the media ducts solely due to capillary forces. It is noted that the media ducts are not illustrated in the cross-sectional views of FIGS. 5 to 7 for reasons of clarity.

FIGS. 7a) and 7b) illustrate two sectional views of the dispensing head 8, used in the apparatus shown in FIG. 1, the section in FIG. 7a) along the transverse direction showing four nozzles 14, whereas the section in FIG. 7b) along the longitudinal direction shows six nozzles 14, so that, again, an overall figure of twenty-four nozzles results. As can be seen in FIGS. 7a) and 7b), a further layer 36 is arranged above the cover layer 30 in the embodiment illustrated, which layer provides enlarged media reservoirs 38 on the one hand and enlarged rising pipes 40 on the other hand. These rising pipes 40, too, become charged with liquid from the media ducts (not illustrated) solely due to capillary forces. Thus, the external reservoirs can very easily be charged using standard pipetting automatic devices, whereas the rising pipes become charged automatically via capillary forces.

The rising pipes 34 and 40, which are open at the top, cause the mass of liquid situated directly above the nozzle to be enlarged. Unlike the liquid in the media ducts 26 and the liquid in the reservoirs 28, the liquid in the rising pipes is accelerated directly in the direction of the nozzle and is coupled to the same via a minimal flow resistance. If, for example, the dispensing head is abruptly decelerated upon a downward movement, for example by the stop 10 shown in FIG. 1, the liquid from the rising pipes 34 and 40 is accelerated directly in the direction of the nozzle exit, whereas the liquid in the reservoirs 28 must first flow, via the media ducts 26, in a direction which is transverse to the direction of acceleration. In doing so, the liquid must overcome a much higher flow resistance.

As has already been explained above, the rising pipes 34 and 40 are adapted such that they are always charged with liquid due to capillary forces. In addition to the embodiments described, wherein every nozzle has its own liquid storage area, it is also possible for several nozzles to form a nozzle group and to be supplied with the same liquid via a common media duct. Further it is possible to assemble several cover plates one above the other so as to increase the packing density of the nozzles, since then the system of the media ducts can be distributed among several levels. By being guided on different levels, these ducts can also seemingly cross one another without a mixing of the different liquids in the respective ducts taking place.

Figure 8:
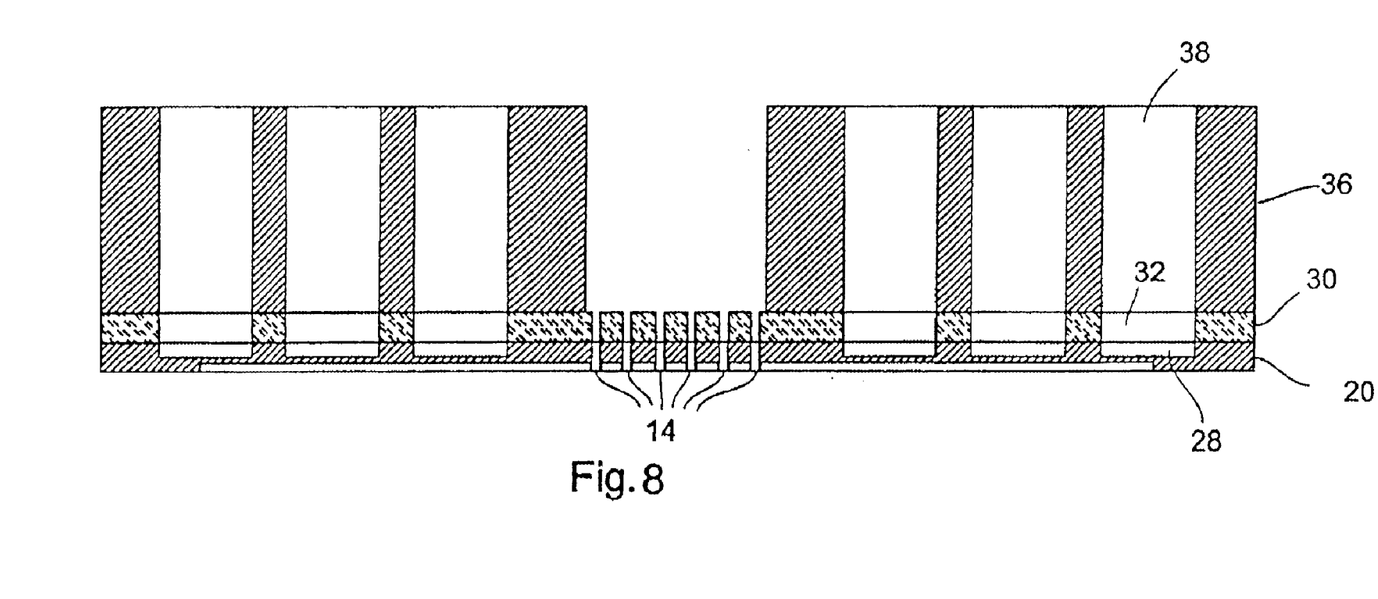

FIG. 8 illustrates a further embodiment of a fluid management apparatus in accordance with the invention, wherein the rising pipes 40 have been omitted as compared to FIG. 7b).

In addition to using the fluid management apparatus in accordance with the invention as a dispensing head, the same may further be advantageously employed so as to realize a format conversion between microtiter plates having different raster schemes. To this end, the patterns of inlet openings and outlet openings may be adapted to different raster schemes of microtiter plates so that a fluid or a liquid can be received from a microtiter plate with a first raster scheme by means of the inlet openings, and the fluid or the liquid can be output to a microtiter plate having a second raster scheme by means of the outlet openings.

The expression "patterns of fluid inlets and fluid outlets" as used herein on the one hand refers to the arrangement of the fluid inlets and outlets while incorporating the spacing of the same toward one another. On the other hand, however, the expression alternatively or additionally relates to the size and/or shape of the fluid inlets and outlets.

What is claimed is:

1. Fluid management apparatus comprising:
   a substrate having a first surface and a second surface which is opposite to the first surface;
   a plurality of fluid inlets which are formed in a first pattern in the first surface of the substrate and comprise first opening cross-sections;
   a plurality of fluid outlets which are formed in a second pattern, which is different from the first pattern, in the second surface of the substrate and comprise second opening cross-sections which are smaller than the first opening cross-sections; and
   a plurality of fluid ducts formed in the substrate, each fluid duct connecting a fluid inlet with a fluid outlet such that each fluid outlet is in fluidic communication with exactly one fluid inlet;
   wherein the first pattern defines spacings between adjacent fluid inlets which are larger than spacings between adjacent fluid outlets defined by the second pattern.

2. Fluid management apparatus as claimed in claim 1, wherein the fluid inlets in the first pattern are arranged in the raster scheme of microtiter plates.

3. Fluid management apparatus as claimed in claim 1, wherein the fluid inlets define fluid reservoirs which are chargeable from the first surface.

4. Fluid management apparatus as claimed in claim 1, wherein the fluid outlets are arranged in a raster in which analytes are to be applied onto a biochip.

5. Fluid management apparatus as claimed in claim 1, wherein the fluid inlets in the first pattern are arranged in a first microtiter plate raster scheme, and wherein the fluid outlets in the second pattern are arranged in a second microtiter plate raster scheme.

6. Fluid management apparatus as claimed in claim 1, wherein the fluid ducts are dimensioned such that a fluid is movable through the same by capillary forces.

7. Fluid management apparatus as claimed in claim 1, wherein the substrate consists of silicon, a silicon-glass compound, a metal or a ceramic.

8. Fluid management apparatus as claimed in claim 1, wherein the substrate consists of a plastic or a polymer.

9. Fluid management apparatus as claimed in claim 1, wherein the substrate comprises several levels and wherein the fluid ducts are distributed among the several levels.

* * * * *